United States Patent [19]

Liu

[11] Patent Number: 4,614,538
[45] Date of Patent: Sep. 30, 1986

[54] HERBICIDAL COMPOSITION
[75] Inventor: Kou-Chang Liu, Wayne, N.J.
[73] Assignee: GAF Corporation, Wayne, N.J.
[21] Appl. No.: 707,300
[22] Filed: Mar. 1, 1985

Related U.S. Application Data

[63] Continuation-in-part of Ser. No. 568,999, Jan. 9, 1984, Pat. No. 4,543,426.

[51] Int. Cl.$^4$ .............................................. E05B 63/14
[52] U.S. Cl. ........................................ 71/121; 564/442
[58] Field of Search .......................... 564/442; 71/121

[56] References Cited

U.S. PATENT DOCUMENTS 4,339,457  7/1982  Plummer et al. ................... 514/427
4,543,426  9/1985  Liu ...................................... 564/442

Primary Examiner—Natalie Trousof
Assistant Examiner—Joseph A. Baska
Attorney, Agent, or Firm—Marilyn J. Maue; Joshua J. Ward

[57] ABSTRACT

A herbicide of the formula:

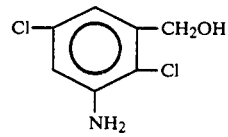

1 Claim, No Drawings

HERBICIDAL COMPOSITION

RELATED APPLICATION

This is a continuation-in-part of my copending application Ser. No. 568,999, filed Jan. 9, 1984, U.S. Pat. No. 4,543,426.

FIELD OF THE INVENTION

The present invention relates to a novel compound which is an inexpensive and active herbicide having high selectivity to soybean and graminae crops including corn, wheat and rice.

DESCRIPTION OF THE PRIOR ART

Certain dichloroanilines have shown generally high activity as plant irradicants and herbicides. Foremost of these are discussed in U.S. Pat. Nos. 3,174,842; 3,332,769; and 4,046,758. However, the herbicidal effectiveness and selectivity of a dihaloaniline having substitution by different functional groups cannot be predicted from an examination of its basic chemical structure or homologous relationship. Often structurally related aromatic compounds have markedly different weed control abilities and crop selectivity.

While many of the dihaloanilines exhibit high plant eradicating properties, they show little if any phytotoxic selectivity for certain commercial crops, such as graminae in either pre-emergence or post-emergence applications. Hence, their range of application is limited unless rates are reduced to such a level that they become ineffectual on certain weed species or repeated applications are required throughout the planting and growing seasons.

Accordingly, it is an object of this invention to provide a herbicide having exceptionally high herbicidal activity in a single application while simultaneously showing good crop selectivity towards commercial graminae crops.

Another object of this invention is to provide a herbicide which can be economically produced and applied to crops in small amounts which are non-contaminating to the soil.

These and other objects will become apparent to those skilled in the art.

SUMMARY OF THE INVENTION

In accordance with the present invention, there is provided a novel herbicidal halogenated hydroxy alkyl aniline having the formula

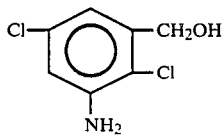

which is 2,5-dichloro-3-hydroxymethyl aniline.

DETAILED DESCRIPTION OF THE INVENTION

The halogenated hydroxymethyl aniline of this invention is preferably prepared by reacting 3-amino-2,5-dichlorobenzoic acid with a suitable reducing agent such as borontrifluoride-tetra-hydrofuran at a temperature of from about 0° to about 50° C. under atmospheric pressure.

The compound of this invention is useful both as pre-emergent and post-emergent herbicide. Among the crops on which the compound may be advantageously employed are, for example, soybean, rice, corn, cotton, wheat, sorghum, peanuts, safflower, beans, peas, carrots, and other cereal crops.

The present dichlorinated hydroxyalkyl aniline may be applied in any amount which will give the required control of weeds. A preferred rate of application of the benzoate is from 0.05 to about 8 lbs. per acre. In practice, the compound may be applied in solid, liquid or in vaporized form, or as an active ingredient in a herbicidal composition or formulation which comprises a carrier and/or a surfactant. A generally accepted carrier is a substance which can be used to dissolve, disperse or diffuse the herbicidal component in the composition. Non-limiting examples of liquid carriers include water, organic solvents such as alcohols, ketones, halogenated hydrocarbons aromatic hydrocarbons, ethers, amides, esters, nitriles, mineral oils, methyl pyrrolidone, polyvinylpyrrolidone and the like. Non-limiting examples of solid carriers include Kaolin, bentonite, talc, diatomaceous earth, vermiculite, clay, gypsum, grain and seed hulls, ground corn cobs and the like. In addition to a carrier, it is usually desirable to add to the composition additives such as emulsifying agents, wetting agents, binding agents, stabilizer and the like. The compounds may be formulated, for example, as a dust, a wettable powder, an emulsifiable concentrate, a granular formulation or an aerosol.

The halogenated hydroxyalkyl aniline herein described may be applied along with plant growth regulators, insecticides, fungicides, nematocides and fertilizers and, if desired, may be applied in combination with one or more other herbicides. Non-limiting examples of other herbicides which can be incorporated with the hydroxyalkyl aniline of this invention are anilides, such as N-methoxymethyl(2,6-diethylphenyl)chloroacetamide; dinitroanilines, such as α,α,α-trifluoro-2,6-dinitro-N,N-di-propyl-p-toluidine; carboxylic acids and derivatives; triazines; substituted ureas; carbamates; thiocarbamates; uracils; heterocycles, organo phosphorous compounds and the like.

Having thus generally described the invention, reference is now had to the following examples which represent preferred embodiments but which are not to be construed as limiting to the scope of the invention as more broadly set forth hereinabove and in the appended claims.

EXAMPLE 1

Preparation of 3-Amino-2,5-Dichlorobenzyl Alcohol

Into a 1 liter three-neck flask was introduced 40 g (0.19 mole) of 3-amino-2,5-dichlorobenzoic acid and 150 ml of tetrahydrofuran. The solution was cooled to 8°–10° C. in an ice bath. A borontrifluoride-tetrahydrofuran (1M) solution (280 ml) was added dropwise over a period of 1 hr. After being stirred at 8° C. for an additional 1 hr. the solution was allowed to warm up slowly to room temperature. The reaction flask was then cooled again in an ice bath and 50 ml of water was added through a dropping funnel. The mixture was taken into 1 liter of methylene chloride and washed once with $NaHCO_3$ and twice with water, then dried over calcium sulfate. The methylene chloride solution afforded 19.2 g of crude solid product, mp 111–121. Five grams of the crude solid was recrystallized from acetonitrile to yield 4.2 g of 3-amino-2,5-dichlorobenzyl alcohol; mp 121–127; nmr (DMSO-d6) δ 4.50 (D, 2H), 5.34 (t, 1H), 5.52 (S, 2H), 6.73 (S, 2H); ir (CHCl$_3$) 3490, 3380, 3240, 1630 and 1598 Cm$^{-1}$.

EXAMPLE 2

Herbicidal Tests

Tests were made on species of representative monocotyledonous and dicotyledonous plants at a rate of 5 lbs/acre, 3-amino-2,5-dichlorobenzyl alcohol in aqueous solution was applied immediately after seeding with plants shown in the following table. The response was evaluated after 2 weeks on a scale of 0 to 9 where 0 represents no injury and 9 represents complete kill.

TABLE I

| Plant Species | Toxicity |
|---|---|
| Weeds | |
| Morning Glory | 8 |
| Mustard | 9 |
| Pigweed | 9 |
| Foxtail | 9 |
| Japanese Millet | 9 |
| Crabgrass | 9 |
| Crops | |
| Soybean | 5 |
| Corn | 6 |
| Wheat | 3 |
| Rice | 5 |

The high toxicity toward weeds and marked selectivity toward crops, particularly wheat, is shown in the above Table.

What is claimed is:

1. A herbicidal composition containing a herbicide of the formula

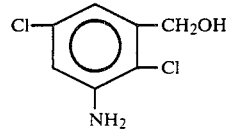

and an inert carrier therefor.

* * * * *